United States Patent [19]

Burch

[11] 4,280,991

[45] Jul. 28, 1981

[54] DIAGNOSTIC COMPOSITIONS

[75] Inventor: William M. Burch, Duffy, Australia

[73] Assignee: Capital Territory Health Commission, Canberra City, Australia

[21] Appl. No.: 928,615

[22] Filed: Jul. 27, 1978

[30] Foreign Application Priority Data

Jul. 29, 1977 [AU] Australia ............................. PD1020

[51] Int. Cl.$^3$ ..................... A61K 49/00; A61K 43/00; G01T 1/00
[52] U.S. Cl. ........................................ 424/1; 128/659; 128/671; 252/305; 252/301.1 R; 424/1.5; 424/9; 424/45; 423/249
[58] Field of Search ................. 424/1, 9, 45; 252/305, 252/301.1 R; 128/2 A, 659, 671; 423/249

[56] References Cited

U.S. PATENT DOCUMENTS

| 3,666,955 | 5/1972 | Suprenant | 424/1 |
| 3,769,967 | 11/1973 | Jones et al. | 128/2 A |
| 3,922,340 | 11/1975 | Miwa | 424/45 |
| 4,158,700 | 6/1979 | Karageozian | 252/301.1 R |

OTHER PUBLICATIONS

Weast, Handbook of Chemistry and Physics, 49th College Edition, Chemical Rubber Co., Cleveland, Ohio, 1968, p. B249.
Taplin et al., Radio Pharmaceuticals, Ed Rhodes et al., Society of Nuclear Medicine, Inc., N.Y., 1975, pp. 305–315.
Bailar et al., Ed., Comprehensive Inorganic Chemistry, vol. 3, Pergamon Press, Oxford, England, 1973, pp. 897–898.
Hawley, Ed., The Condensed Chemical Dictionary, 8th Ed., Van Nostrand Reinhold Co., NY, 1971, pp. 848–849.

Primary Examiner—Benjamin R. Padgett
Assistant Examiner—Christine M. Nucker
Attorney, Agent, or Firm—Cushman, Darby & Cushman

[57] ABSTRACT

The invention discloses diagnostic compositions for use in obtaining images of a patient's lungs. The basic components of the composition of the invention are sodium pertechnetate which is radioactive and ethanol. This composition may be combusted and the resulting products cooled or alternatively the composition may be inserted into a pressure vessel with an aerosol. In both cases a gas like mixture results. A particular advantage is that a patient is able to breath the mixture of the invention in a normal way and does not need to undergo any training in inhalation.

2 Claims, No Drawings

DIAGNOSTIC COMPOSITIONS

FIELD OF THE INVENTION

This invention relates to compositions for use in diagnosis, the method of production of the compositions and the method of use of the compositions.

Specifically the field of interest of this invention is the diagnosis of abnormalities in the Human Lung, and more specifically those abnormalities which give rise to changes in the pattern of distribution of air during normal (tidal) breathing.

DESCRIPTION OF THE PRIOR ART

Classical tools for non-invasive assessment of lung pathology are stethoscopes and chest x-rays. In the clinical situation where blood supply to a region of the lung becomes obstructed (pulmonary embolus) these tools are unhelpful except for excluding an infiltrative growth of some considerable size or other gross pathology.

A much more definitive but extremely unpleasant procedure for the patient is a bronchogram. This is a chest x-ray following the dispersion of an Iodine laden contrast medium into the major airways of the lungs. The medium absorbs x-rays strongly to demonstrate patency of the airways.

The advent of radio-active gases, and technology to image their distribution throughout the lungs, (the Gamma Camera) has led to some improvement in the diagnostic accuracy of lung pathology. Ventilation (airways) and perfusion (blood supply) imaging of the lungs with radionuclides provide the examination for choice for acute pulmonary embolus.

However, the only radio-active gas generally available is Xenon-133. It has certain serious limitations compared with an ideal ventilation imaging agent. These include radiation dose to the patient which restricts practical application to one view per patient (usually posterior) whereas all four views are desirable. Also the low energy (80 kev) of xenon gamma rays compromises the resolving capability of the Gamma Camera.

More recently, workers in the U.S.A. and elsewhere have created a radio-active aqueous aerosol using well-established nebulizing techniques. In this procedure, the same radio-nuclide, Technetium$-^{99m}$, as used for the perfusion study, can be nebulised (formed into an aerosol) and breathed by the patient to form an airways distribution pattern capable of being displayed on a Gamma Camera.

Two major disadvantages of the Xenon system listed above are overcome with aerosols, in that all four views are readily obtainable and the Gamma Ray energy is ideal for the image taking process.

However, another very pertinent drawback still limits full realisation of ventilation imaging. This is that the aerosol nebulisation technique requires heavy deep breathing through a mouthpiece for about five (5) minutes. This manoeuvre is physically impossible for some patients and distressing for many others. In addition, there is a high level of wastage of radio-nuclide. Only about 10% of the dose in the nebuliser actually gets into the lungs. The rest plates out in the apparatus and the patient's major airways, increasing radiation dose to the patient and attending staff.

Contaminated apparatus must then be stored for a day or so prior to washing to allow the radiation to decay to an insignificant level.

BRIEF SUMMARY OF THE INVENTION

It is a prime object of this invention to provide a composition of matter which may be used to produce an aerosol or a dispersion containing radio active material in very small quantities, which aerosol or dispersion may be readily breathed during normal tidal breathing.

Broadly this invention provides a composition of matter comprising a solution containing an alkali metal pertechnetate, desirably sodium pertechnetate ($Na_2{}^{99m}TcO_4$) in ethyl alcohol with or without water. Preferably the alcohol is absolute ethyl alcohol. The invention also includes a propellant composition composed of the alcoholic solution of sodium pertechnetate and a suitable propellant and also a dispenser containing the propellant composition.

DETAILED DESCRIPTION

Preferably the manner of production and manner of use may be as follows:

Sodium pertechnetate $-^{99m}(Na_2{}^{99m}TcO_4)$ in physiological saline—the standard radionuclide used in Nuclear Medicine facilities—is evaporated to dryness. Absolute ethyl alcohol is added to the residue and the mixture thoroughly stirred. About seventy percent of the original $^{99m}Tc$ activity is retained in solution in the alcohol—whatever initial activity or alcohol volume is used (within practical limits).

An aliquot of this solution is transferred to a small pressure vessel to occupy about 40% of the vessel's volume. The remaining volume is filled with a mixture of "Freon" (Registered Trade Mark) liquified gas (F12 and F114) to give a suitable propellant pressure around 30 p.s.i.

The pressure vessel is capped with a $50\mu l$ metered dose valve as used in standard medical inhalers. The whole process of delivery of the radio-aerosol is the same as conventional aerosol drug inhalation via "Medihaler" type dispensers.

The whole process can be undertaken at a centralised radiopharmaceutical production unit and complete disposable aerosol packs distributed to Nuclear Medicine facilities on a daily basis for lung ventilation procedures. This is standard practice for other routine radiopharmaceutical preparations.

In lieu of introducing the pertechnetate as alcoholic aerosol via propellant, the radio-active alcoholic solution may be combusted and the cooled products of combustion inhaled by the patient from a simple container. On combustion of the alcoholic pertechnetate solution it is believed that a microscopic suspension of pertechnetate in carbon dioxide, water vapour and air is created, and which behaves like a gas which is easily inhaled by the patient.

Radio-aerosol inhalation by these methods overcome the drawbacks of all existing systems in that the patient will need only a few brief puffs during normal tidal breathing to get adequate, reproducible and controlled airways deposition. There is minimal wastage, radiation shielding is straight forward, and no rehearsal or patient education is required.

In one particular use 4.5 millicuries (mCi) of sodium pertechnetate in 0.4 ml of a 0.9% saline solution was evaporated to dryness and then 0.5 ml of 95% ethyl alcohol was added. The supernatant liquid approximately 0.3 ml containing approximately 3.2 mCi of sodium pertechnetate was collected on a syringe and inserted into a pressure vessel, to which was added 0.9 ml of Freon to give a propellant of pressure about 30 p.s.i.

In the foregoing description, sodium pertechnetate has been illustrated. However it is observed that other non-toxic alkali metal pertechnetates as are known to those skilled in the art may be used. Additionally, the pertechnetate used need not be in saline solution. Further, suitable propellants other than $F_{12}$ and $F_{114}$ and their mixtures may be used if desired.

As mentioned before, Freon is a trade mark and as used in this specification is intended to encompass a group of halogenated hydrocarbons (usually based on methane) containing one or more fluorine atoms which are useful for propellants. Thus by $F_{12}$ is meant the propellant, dichlorodifluoromethane ($CCl_2F_2$) and by $F_{114}$ is meant the propellant (dichlorotetrafluoroethane) ($CCl_2CF_4$).

Thus in a further embodiment the invention comprises a propellant composition consisting of an alkali metal pertechnetate, preferably sodium pertechnetate, ethyl alcohol and a propellant. Preferably the propellant is a halogenated hydrocarbon and more preferably $F_{12}$ and/or $F_{114}$.

It should be remembered that the quantities of pertechnetate used are extremely small and 1 nanogram ($10^{-9}$) of sodium pertechnetate is a 5 mCi dose. On a weight basis the preferred solution contains 1 to 3 parts of sodium pertechnetate per million parts of ethyl alcohol.

What we claim is:

1. A method of forming a composition for use in lung examination comprising combusting a solution consisting essentially of an alkali metal pertechnetate and ethyl alcohol and cooling the products of combustion.

2. A method for introducing radionuclides into the lungs of a patient for lung examination comprising the steps of:
    (i) combusting a composition consisting essentially of alkali metal pertechnetate dissolved in ethyl alcohol;
    (ii) cooling the resulting product; and
    (iii) inhaling the same.

* * * * *